(12) United States Patent
Kobara Pestell et al.

(10) Patent No.: US 7,987,539 B2
(45) Date of Patent: Aug. 2, 2011

(54) FUNGICIDAL DETERGENT COMPOSITIONS

(75) Inventors: Elizabeth Harumi Kobara Pestell, La Croix s/Lutry (CH); Marcel Schnyder, Basel (CH); François Brugger, Waltenheim (FR); Fernand Hoffstetter, Ranspach-le-Bas (FR)

(73) Assignee: BASF SE Ludwigshafen (DE)

( * ) Notice: Subject to any disclaimer, the term of this patent is extended or adjusted under 35 U.S.C. 154(b) by 103 days.

(21) Appl. No.: 10/593,227

(22) PCT Filed: Mar. 14, 2005

(86) PCT No.: PCT/EP2005/051133
§ 371 (c)(1),
(2), (4) Date: Sep. 18, 2006

(87) PCT Pub. No.: WO2005/089552
PCT Pub. Date: Sep. 29, 2005

(65) Prior Publication Data
US 2008/0058393 A1 Mar. 6, 2008

(30) Foreign Application Priority Data
Mar. 23, 2004 (EP) ..................... 04101198

(51) Int. Cl.
*C11D 3/48* (2006.01)
*A01H 5/02* (2006.01)

(52) U.S. Cl. .......................... 8/147; 510/382

(58) Field of Classification Search .............. 510/382; 8/147
See application file for complete search history.

(56) References Cited

U.S. PATENT DOCUMENTS

| | | | | |
|---|---|---|---|---|
| 3,506,720 A | 4/1970 | Model et al. | | 260/613 |
| 3,576,843 A | 4/1971 | Model et al. | | 260/479 |
| 3,642,872 A | 2/1972 | Model et al. | | 260/479 |
| 3,784,694 A * | 1/1974 | Basel et al. | | 514/522 |
| 3,784,698 A | 1/1974 | Model et al. | | 424/311 |
| 3,903,007 A | 9/1975 | Model et al. | | 252/106 |
| 4,118,332 A * | 10/1978 | Apostolatos et al. | | 514/164 |
| 4,906,648 A * | 3/1990 | Minami et al. | | 514/365 |
| 6,090,399 A * | 7/2000 | Ghosh et al. | | 424/409 |
| 6,228,127 B1 | 5/2001 | Reinehr et al. | | |
| 6,365,563 B1 | 4/2002 | Hirsch et al. | | 510/319 |
| 2003/0212232 A1 * | 11/2003 | Majeti et al. | | 528/10 |
| 2004/0261196 A1 * | 12/2004 | Ghosh et al. | | 8/147 |

FOREIGN PATENT DOCUMENTS
JP      11515049 T      12/1999

OTHER PUBLICATIONS

English Language Derwent Abstract AN 1982-69061E [33] (XP-002306551) for JP 57 109898 (Jul. 8, 1982).
English Language Derwent Abstract AN 2003-535514 [51] (XP-002306552) for JP 2002 187803 (Jul. 5, 2002).
English Language Derwent Abstract AN 2002-475017 [51] (XP-002306553) for JP 2002 105855 (Apr. 10, 2002).
English Language Derwent Abstract AN 1994-011756 [02] (XP-002330000) for JP 05 318635 (Dec. 3, 1993).
English Language Derwent Abstract AN 1993-224235/28 (XP-002330000) for JP 05 148109 (Jun. 15, 1993).

* cited by examiner

Primary Examiner — Milton I Cano
Assistant Examiner — Thuy-Ai N Nguyen
(74) Attorney, Agent, or Firm — Shiela A. Loggins

(57) ABSTRACT

Disclosed is the use of the compound of formula

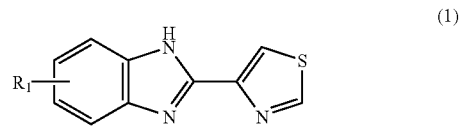

(1)

wherein
$R_1$ is hydrogen; or $C_1$-$C_5$alkyl
for the fungicidal treatment of hard surfaces and textile fiber materials.
The compounds of formula (1) impart antifungal properties to washed textile material. Bacteria that get on the textile material while it is being worn are destroyed.

11 Claims, No Drawings

FUNGICIDAL DETERGENT COMPOSITIONS

The present invention relates to fungicidal detergent compositions and to the use of such compositions for the fungicidal treatment of hard surfaces and textile fibre materials.

Under high humid conditions and warm temperatures, fungi develop damp and unpleasant odors on fabrics. Some fungi species as *Chaetomium globosum* are known to produce geosmin, a volatile organic compound with a distinct "earthy" odor.

Some discoloration can occur due to the formation of masses of colored spores. Changes in the color fabric are caused by acids and other substances produced by fungi.

Mildewed areas are colored from green to shades of brown and deep black. *Chaetomium globosum*, a very common fungus related with occurrence of mildew on fabrics, produces dark grayish green stains on fabrics. The pigment formation is also caused by the acids produced by the action of mildew on cellulose, soil and other food substances present on the fabric.

Enzymes produced by fungus can lead to the fabric deterioration and rot. Some species are known for being cellulose eaters like *Chaetomium globosum*.

Cleaning and disinfectant compositions comprising fungicidal active ingredients, e.g. hand and machine dishwashing formulations, cleaning and disinfecting formulations for hard surfaces and liquid and solid textile washing formulations, are therefore becoming ever more widespread. The fungicidal action and dust mites growth control is more and more a required demand for such formulations.

It has now surprisingly been found that detergent compositions comprising as fungicidal active the compound of formula

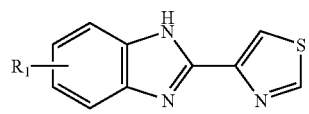

(1)

wherein
$R_1$ is hydrogen; or $C_1$-$C_5$alkyl;
exhibit strong fungicidal effects for hard surfaces and textile materials.

The present invention therefore refers to the use of the compound of formula (1) for the fungicidal treatment of hard surfaces and textile fibre materials.

Preferably, in formula (1) $R_1$ is hydrogen (1H-Benzimidazole, 2-(4-Thiazolyl)-; Thiabenda-zol).

The present invention accordingly relates to a detergent composition comprising
(a) 0.01 to 90% by weight of a compound of formula (1);
(b) 1 to 80% by weight of one or more synthetic detergents or of a soap or of combinations of the mentioned substances;
(c) 0-75% of a builder;
(d) 0-30% by weight of a peroxide;
(e) 0-10% by weight of a bleach activator;
(f) 0 to 50% by weight of one or more hydrotropic agents,
(g) 0 to 50% by weight of an alcohol,
(h) 0 to 80% by weight of a fabric softening component; and
(f) tap water or deionized water ad 100%.

Preferably, the present invention accordingly relates to a detergent composition comprising
(a) 0.01 to 10% by weight of a compound of formula (1);
(b) 5 to 70% by weight of one or more synthetic detergents or of a soap or of combinations of the mentioned substances and/or of a salt of a saturated and/or unsaturated $C_8$-$C_{22}$ fatty acid,
(f) 0 to 50% by weight of one or more hydrotropic agents,
(g) 0 to 50% by weight of an alcohol,
(h) 0 to 80% by weight of a fabric softening component; and optionally
(i) tap water or deionised water ad 100%.

As component (b), anionic, nonionic, or zwitterionic and amphoteric synthetic detergents are suitable.

Suitable anionic detergents are
sulfates, for example fatty alcohol sulfates, the alkyl chain of which has from 8 to 18 carbon atoms, for example sulfated lauryl alcohol;
fatty alcohol ether sulfates, for example the acid esters or salts thereof of a polyaddition product of from 2 to 30 mol of ethylene oxide and 1 mol of a $C_8$-$C_{22}$ fatty alcohol;
the alkali metal, ammonium or amine salts, referred to as soaps, of $C_8$-$C_{20}$ fatty acids, for example coconut fatty acid;
alkylamide sulfates;
alkylamine sulfates, for example monoethanolamine lauryl sulfate;
alkylamide ether sulfates;
alkylaryl polyether sulfates;
monoglyceride sulfates;
alkanesulfonates, the alkyl chain of which contains from 8 to 20 carbon atoms, for example dodecyl sulfonate;
alkylamide sulfonates;
alkylaryl sulfonates;
α-olefin sulfonates;
sulfosuccinic acid derivatives, for example alkyl sulfosuccinates, alkyl ether sulfo-succinates or alkylsulfosuccinamide derivatives;
N-[alkylamidoalkyl]amino acids of formula

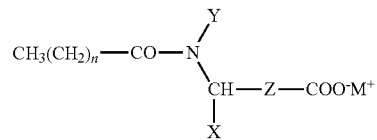

wherein
X is hydrogen, $C_1$-$C_4$alkyl or —COO$^-$M$^+$,
Y is hydrogen or $C_1$-$C_4$alkyl,
Z is —(CH$_2$)$_{m_1-1}$
$m_1$ is from 1 to 5,
$n_1$ is an integer from 6 to 18 and
M is an alkali metal cation or amine cation,
alkyl and alkylaryl ether carboxylates of formula (13)
CH$_3$—X—Y-A wherein
X is a radical of formula —(CH$_2$)$_{5-19}$—O—,

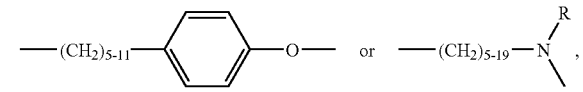

R is hydrogen or $C_1$-$C_4$alkyl,
Y is —(CHCHO)$_{1-50}$—,
A is (CH$_2$)$_{m2-1}$—COO$^-$M$^+$ or

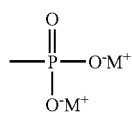

$m_2$ is from 1 to 6 and

M is an alkali metal cation or amine cation.

Also used as anionic surfactants are fatty acid methyl taurides, alkyl isothionates, fatty acid polypeptide condensation products and fatty alcohol phosphoric acid esters. The alkyl radicals occurring in those compounds preferably have from 8 to 24 carbon atoms.

The anionic surfactants are generally in the form of their water-soluble salts, such as the alkali metal, ammonium or amine salts. Examples of such salts include lithium, sodium, potassium, ammonium, triethylamine, ethanolamine, diethanolamine and triethanolamine salts. The sodium, potassium or ammonium ($NR_1R_2R_3$) salts, especially, are used, with $R_1$, $R_2$ and $R_3$ each independently of the others being hydrogen, $C_1$-$C_4$alkyl or $C_1$-$C_4$hydroxyalkyl.

Especially preferred anionic surfactants in the composition according to the invention are monoethanolamine lauryl sulfate or the alkali metal salts of fatty alcohol sulfates, especially sodium lauryl sulfate and the reaction product of from 2 to 4 mol of ethylene oxide and sodium lauryl ether sulfate.

Suitable zwitterionic and amphoteric surfactants include $C_8$-$C_{18}$betaines, $C_8$-$C_{18}$sulfobetaines, $C_8$-$C_{24}$alkylamido-$C_1$-$C_4$alkylenebetaines, imidazoline carboxylates, alkylamphocarboxycarboxylic acids, alkylamphocarboxylic acids (e.g. lauroamphoglycinate) and N-alkyl-β-aminopropionates or -iminodipropionates, with preference being given to $C_{10}$-$C_{20}$alkylamido-$C_1$-$C_4$akylenebetaines and especially to coconut fatty acid amide propylbetaine.

Nonionic surfactants that may be mentioned include, for example, derivatives of the adducts of propylene oxide/ethylene oxide having a molecular weight of from 1000 to 15 000, fatty alcohol ethoxylates (1-50 EO), alkylphenol polyglycol ethers (1-50 EO), polyglucosides, ethoxylated hydrocarbons, fatty acid glycol partial esters, for example diethylene glycol monostearate, fatty acid alkanolamides and dialkanolamides, fatty acid alkanolamide ethoxylates and fatty amine oxides.

As component (b) there may also be used the salts of saturated and unsaturated $C_8$-$C_{22}$ fatty acids either alone or in the form of a mixture with one another or in the form of a mixture with other detergents mentioned as component (b). Examples of such fatty acids include, for example, capric, lauric, myristic, palmitic, stearic, arachidic, behenic, caproleic, dodecenoic, tetradecenoic, octadecenoic, oleic, eicosenoic and erucic acid, and the commercial mixtures of such acids, such as, for example, coconut fatty acid. Such acids are present in the form of salts, there coming into consideration as cations alkali metal cations, such as sodium and potassium cations, metal atoms, such as zinc and aluminium atoms, and nitrogen-containing organic compounds of sufficient alkalinity, such as amines and ethoxylated amines. Such salts may also be prepared in situ.

The builder component (c) may be an alkali metal phosphate, especially a tripolyphosphate; a carbonate or bicarbonate, especially the sodium salts thereof; a silicate or disilicate; an aluminosilicate; a polycarboxylate; a polycarboxylic acid; an organic phosphonate; or an aminoalkylene poly (alkylene phosphonate); or a mixture of these.

Preferred silicates are crystalline layered sodium silicates of the formula $NaHSi_mO_{2m+1} \cdot pH_2O$ or $Na_2Si_mO_{2m+1} \cdot pH_2O$ in which m is a number from 1.9 to 4 and p is 0 to 20.

Preferred aluminosilicates are the commercially-available synthetic materials designated as Zeolites A, B, X, and HS, or mixtures of these. Zeolite A is preferred.

Preferred polycarboxylates include hydroxypolycarboxylates, in particular citrates, polyacrylates and their copolymers with maleic anhydride.

Preferred polycarboxylic acids include nitrilotriacetic acid and ethylene diamine tetra-acetic acid.

Preferred organic phosphonates or aminoalkylene poly (alkylene phosphonates) are alkali metal ethane 1-hydroxy diphosphonates, nitrilo trimethylene phosphonates, ethylene diamine tetra methylene phosphonates and diethylene triamine penta methylene phosphonates.

The amount of builders is preferably 5-70% by weight, preferably 5-60% by weight and more preferably 10-60% by weight. As to the builders it is preferred that the lower limit is 15% by weight, especially 20% by weight.

Suitable peroxide components (d) include, for example, the organic and inorganic peroxides (like sodium peroxides) known in the literature and available commercially that bleach textile materials at conventional washing temperatures, for example at from 5 to 95° C. In particular, the organic peroxides are, for example, monoperoxides or polyperoxides having alkyl chains of at least 3, preferably 6 to 20, carbon atoms; in particular diperoxy-dicarboxylates having 6 to 12 C atoms, such as diperoxyperazelates, diperoxypersebacates, diperoxyphthalates and/or diperoxydodecanedioates, especially their corresponding free acids, are of interest. It is preferred, however, to employ very active inorganic peroxides, such as persulphate, perborate and/or percarbonate. It is, of course, also possible to employ mixtures of organic and/or inorganic peroxides.

The amount of peroxide is preferably 0.5-30% by weight, preferably 1-20% by weight and more preferably 1-15% by weight. In case a peroxide is used, the lower limit is preferably 2% by weight, especially 5% by weight.

The peroxides, especially the inorganic peroxides, are preferably activated by the inclusion of a bleach activator (component (e)). Preferred are such compounds that, under perhydrolysis conditions, yield unsubstituted or substituted perbenzo- and/or peroxo-carboxylic acids having from 1 to 10 carbon atoms, especially from 2 to 4 carbon atoms. Suitable compounds include those that carry O- and/or N-acyl groups having the said number of carbon atoms and/or unsubstituted or substituted benzoyl groups. Preference is given to polyacylated alkylenediamines, especially tetraacetylethylenediamine (TAED), acylated glycolurils, especially tetraacetylglycoluril (TAGU), N,N-diacetyl-N,N-dimethylurea (DDU), acylated triazine derivatives, especially 1,5-diacetyl-2,4-dioxohexahydro-1,3,5-triazine (DADHT), compounds of formula

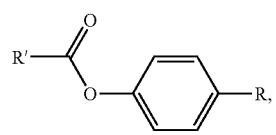

wherein R' is a sulfonate group, a carboxylic acid group or a carboxylate group, and wherein R' is linear or branched ($C_7$-$C_{15}$)alkyl; also activators that are known under the names SNOBS, SLOBS, NOBS and DOBA, acylated polyhydric alcohols, especially triacetin, ethylene glycol diacetate and 2,5-diacetoxy-2,5-dihydrofuran and acetylated sorbitol and mannitol and acylated sugar derivatives, especially pentaacetylglucose (PAG), sucrose polyacetate (SUPA), pentaacetylfructose, tetraacetylxylose and octaacetyllactose, and acetylated, optionally N-alkylated, glucamine and gluconolactone. The combinations of conventional bleach activators disclosed in German Patent Application DE-A-44 43 177 may also be used. Nitrile compounds that form peroxyimidic acids with peroxides are also suitable as bleach activators. Preferred are tetraacetyl ethylenediamine and nonoyloxybenzene sulfonate.

The amount of bleach activator is preferably 0-10% by weight, preferably 0-8% by weight. In case a bleach activator is used, the lower limit is preferably 0.5% by weight, especially 1% by weight.

Bleaching catalysts, which may be added, include, e.g., enzymatic peroxide precursors and/or metal complexes. Preferred metal complexes are manganese, cobalt or iron complexes such as manganese or iron phthalocyanines or the complexes described in EP-A-0509787. In case a bleaching catalyst is used the amount is preferably 0.005 to 2% by weight, more preferably 0.01 to 2% by weight, especially 0.05 to 2% by weight. Highly preferred is an amount of 0.1-2% by weight.

As examples for bleaching catalysts the following are mentioned:

WO-A-95/30681 (see i.e. formula (I) and the following definition on page 1, lines 7 to 30; especially formula (I) and the following definitions given on page 2, lines 29 to page 11, line 11). Preferred ligands are those given on page 13, line 12 to page 26, line 11.

WO-A-01/09276 (see i.e. formulae (1), (2) and (3) and the following definitions given on pages 2 and 3).

WO-A-01/05925 (see i.e. formula (1) and the following definition on page 1, last paragraph to page 2, first paragraph. The preferences given for the metal complexes apply, see especially those of formula (2) on page 3 and those of formula (3) on page 4).

WO-A-02/088289 (see i.e. formula (1) and the following definition on page 2. The preferences given for the metal complexes apply, see especially the ligands of formula (3) and also the preferences given on page 3, fourth paragraph to page 4, paragraph 7).

The following compounds are suitable as component (f):

sulfonates of terpenoids, or of mono- or di-nuclear aromatic compounds, for example sulfonates of camphor, toluene, xylene, cumene or of naphthol;

saturated or unsaturated $C_3$-$C_{12}$ di- or poly-carboxylic acids, for example malonic, succinic, glutaric, adipic, pimelic, suberic, azelaic and sebacic acid, undecane- and dodecane-dioic acid, fumaric, maleic, tartaric and malic acid, and citric and aconitic acid;

aminocarboxylic acids, such as ethylenediaminetetraacetic acid, hydroxyethylethylene-diaminetetraacetic acid and nitrilotriacetic acid;

cycloaliphatic carboxylic acids, such as camphoric acid;

aromatic carboxylic acids, such as benzoic, phenylacetic, phenoxyacetic and cinnamic acid, 2-, 3- and 4-hydroxybenzoic acid, anilic acid, and o-, m- and p-chlorophenylacetic acid and o-, m- and p-chlorophenoxyacetic acid;

isethionic acid;
tannic acid;
acid amides of formula

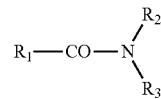

wherein
$R_1$ is hydrogen or $C_1$-$C_{12}$alkyl and
$R_2$ and $R_3$ are each independently of the other hydrogen, $C_1$-$C_{12}$alkyl, $C_2$-$C_{12}$alkenyl, $C_2$-$C_{12}$hydroxyalkenyl, $C_2$-$C_{12}$hydroxyalkyl or a polyglycol ether chain having from 1 to 30 —$CH_2$—$CH_2$—O— or —$CHY_1$—$CHY_2$—O— groupings, wherein one of the radicals $Y_1$ and $Y_2$ is hydrogen and the other is methyl, such as N-methylacetamide;

urea derivatives of formula

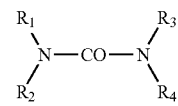

wherein
$R_1$, $R_2$, $R_3$ and $R_4$ are each independently of the others hydrogen, $C_1$-$C_8$alkyl, $C_2$-$C_8$alkenyl, $C_1$-$C_8$hydroxyalkyl or $C_2$-$C_8$hydroxyalkenyl.

All the organic acids mentioned under (f) can also be in the form of their water-soluble salts, such as the alkali metal salts, especially the sodium or potassium salts, or the amine ($NR_1R_2R_3$) salts wherein
$R_1$, $R_2$ and $R_3$ are each independently of the others hydrogen, $C_1$-$C_8$alkyl, $C_2$-$C_8$alkenyl, $C_1$-$C_8$hydroxyalkyl, $C_5$-$C_8$cycloalkyl or polyalkyleneoxy-$C_1$-$C_{18}$alkyl or
$R_1$, $R_2$ and $R_3$, together with the nitrogen atom to which they are bonded, are unsubstituted or $C_1$-$C_4$alkyl-substituted morpholino.

Component (f) can consist of a single compound or a plurality of different compounds.

Very special preference is given to a combination of cumenesulfonate and citric acid monohydrate.

As component (g) there come into consideration as dihydric alcohols especially those compounds having from 2 to 6 carbon atoms in the alkylene moiety, such as ethylene glycol, 1,2- or 1,3-propanediol, 1,3-, 1,4- or 2,3-butanediol, 1,5-pentanediol and 1,6-hexanediol.

Preference is given to 1,2-propanediol (propylene glycol).

Preferred monohydric alcohols are ethanol, n-propanol and isopropanol and mixtures of those alcohols.

Preferred detergent compositions according to the present invention, especially useful for the fungicidal treatment of textile fibre materials comprise
(a) 0.01-5% of a compound of formula (1);
(b) 1-70% of an anionic surfactant and/or a nonionic surfactant;
(c) 0-75% of a builder;
(d) 0-30% of a peroxide; and
(e) 0-10% of a peroxide activator;
and most preferably
(a) 0.01-5% of a compound of formula (1);
(b) 5-70% of an anionic surfactant and/or a nonionic surfactant;

(c) 5-70% of a builder;

(d) 0.5-30% of a peroxide; and (e) 0.5-10% of a peroxide activator and/or 0.1-2% of a bleaching catalyst.

Furthermore, the detergent optionally contains enzymes. Enzymes can be added to detergents for stain removal. The enzymes usually improve the performance on stains that are either protein- or starch-based, such as those caused by blood, milk, grass or fruit juices. Preferred enzymes are cellulases, proteases, amylases and lipases. Preferred enzymes are cellulases and proteases, especially proteases. Cellulases are enzymes which act on cellulose and its derivatives and hydrolyze them into glucose, cellobiose, cellooligosaccharide. Cellulases remove dirt and have the effect of mitigating the roughness to the touch. Examples of enzymes to be used include, but are by no means limited to, the following:

- proteases as given in U.S. Pat. No. 6,242,405, column 14, lines 21 to 32;
- lipases as given in U.S. Pat. No. 6,242,405, column 14, lines 33 to 46;
- amylases as given in U.S. Pat. No. 6,242,405, column 14, lines 47 to 56; and
- cellulases as given in U.S. Pat. No. 6,242,405, column 14, lines 57 to 64.

The enzymes can optionally be present in the detergent. When used, the enzymes are usually present in an amount of 0.01-5% by weight, preferably 0.05-5% and more preferably 0.1-4% by weight, based on the total weight of the detergent.

The composition according to the invention may additionally comprise (k) an antimicrobial agent selected from 2-hydroxy-diphenyl ether of formula

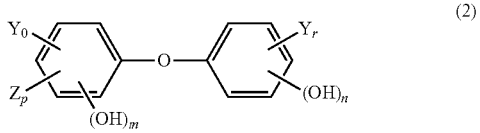

(2)

wherein

Y is chlorine or bromine,

Z is $SO_2H$, $NO_2$ or $C_1$-$C_4$alkyl, r is from 0 to 3, o is from 0 to 3, p is 0, 1 or 2, m is 1 or 2 and n is 0 or 1, and more especially a compound of formula

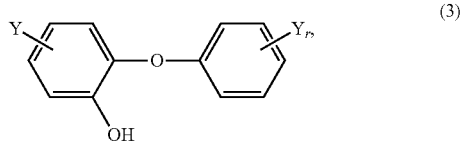

(3)

wherein

Y is chlorine and r is 1 or 2.

Very special preference is given to a compound of formula

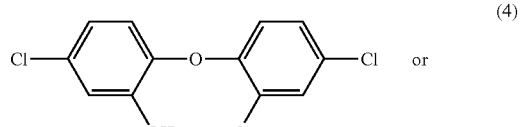

(4)

or

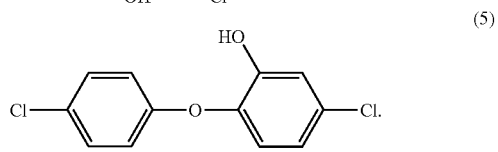

(5)

The present invention therefore relates to a detergent composition, preferably for the fungicidal treatment of hard surfaces comprising (a) 0.01 to 90% by weight of a compound of formula (1) according to claim 1;

(b) 1 to 80% by weight of one or more synthetic detergents or of a soap or of combinations of the mentioned substances;

(f) 0 to 50% by weight of one or more hydrotropic agents, (g) 0 to 50% by weight of an alcohol, (k) 0.00 to 50% by weight of an antimicrobial agent selected from 2-hydroxy-diphenyl ether of formula (2); and (i) tap water or deionized water ad 100%.

The compounds of formula (1) are preferably used as fungicidal agent in laundry compositions.

Therefore, the present invention relates to a process for the domestic washing and fungicidal treatment of a textile fibre material wherein the textile fibre material is contacted with an aqueous solution of a detergent composition comprising a compound of formula (1). Preferably, the detergent composition contains at least one enzyme selected from the group consisting of cellulase, protease, amylase and lipase, and the temperature of the solution is between 5° C. and 40° C., preferably between 5° C. and 30° C., throughout the process.

Further preferred additives for the detergents according to the invention are polymers that, during the washing of textiles, inhibit staining caused by dyes in the washing liquor that have been released from the textiles under the washing conditions (dye fixing agents, dye transfer inhibitors). Such polymers are preferably polyvinylpyrrolidones, polyvinylimidazoles or polyvinylpyridine N-oxides which may have been modified by the incorporation of anionic or cationic substituents, especially those having a molecular weight in the range from 5000 to 60 000, more especially from 10 000 to 50 000. Such polymers are usually used in an amount of from 0.01 to 5%, preferably 0.05 to 5% by weight, especially 0.1 to 2% by weight, based on the total weight of the detergent. Preferred polymers are those given in WO-A-02/02865 (see especially page 1, last paragraph and page 2, first paragraph).

The detergents used will usually contain one or more auxiliaries such as soil suspending agents, for example sodium carboxymethylcellulose; salts for adjusting the pH, for example alkali or alkaline earth metal silicates; foam regulators, for example soap; salts for adjusting the spray drying and granulating properties, for example sodium sulphate; perfumes; and also, if appropriate, antistatic and softening agents; such as smectite clays; photobleaching agents; pigments; and/or shading agents. These constituents should, of course, be stable to any bleaching system employed. Such auxiliaries can be present in an amount of, for example, 0.1 to 20% by weight, preferably 0.5 to 10% by weight, especially 0.5 to 5% by weight, based on the total weight of the detergent.

The detergent compositions can take a variety of physical forms including powder, granular, tablet and liquid forms. Examples thereof are conventional powder heavy-duty detergents, compact and supercompact heavy-duty detergents and tablets, like heavy-duty detergent tablets. One important physical form is the so-called concentrated granular form adapted to be added to a washing machine.

Of importance are also the so-called compact (or supercompact) detergents. In the field of detergent manufacture, a trend has developed recently towards the production of compact detergents, which contain increased amounts of active substance. In order to minimize energy expenditure during the washing process, the compact detergents are required to operate efficiently at temperatures as low as 40° C., or even at room temperatures, e.g. at 25° C. Such detergents usually contain only low amounts of fillers or processing aids, like sodium sulfate or sodium chloride. The amount of such fillers is usually 0-10% by weight, preferably 0-5% by weight, especially 0-1% by weight, based on the total weight of the detergent. Such detergents usually have a bulk density of 650-1000 g/l, preferably 700-1000 g/l and especially 750-1000 g/l.

The detergents can also be present in the form of tablets. Relevant characteristics of tablets are ease of dispensing and convenience in handling. Tablets are the most compact delivery of solid detergents and have a bulk density of, for example, 0.9 to 1.3 kg/litre. To enable fast disintegration laundry detergent tablets generally contain special disintegrants:

Effervescents such as carbonate/hydrogencarbonate/citric acid;

swelling agents like cellulose, carboxymethyl cellulose, cross-linked poly(N-vinylpyrrollidone);

quickly dissolving materials such as Na (K) acetate, or Na (K) citrate;

rapidly dissolving water-soluble rigid coating such as dicarboxy acids.

The tablets can also contain combinations of any of the above disintegrants.

The detergent may also be formulated as an aqueous liquid comprising 5-50, preferably 10-35% water or as a non-aqueous liquid detergent, containing not more than 5, preferably 0-1 wt. % of water. Non-aqueous liquid detergent compositions can contain other solvents as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% of such carriers. The detergents can also be present as the so-called "unit liquid dose" form.

This detergent treatment of textiles can be conducted as a domestic treatment in normal washing machines.

The textile fibres treated with the process of the present invention may be natural or synthetic fibres or mixtures thereof. Examples of natural fibres include vegetable fibres such as cotton, viscose, flax, rayon or linen, preferably cotton and animal fibres such as wool, mohair, cashmere, angora and silk, preferably wool. Synthetic fibres include polyester, polyamide and polyacrylonitrile fibres. Preferred textile fibres are cotton, polyamide and wool fibres, especially cotton fibres. Preferably, textile fibres treated according to the method of the present invention have a density of less than 200 g/m$^2$.

According to this process usually an amount of 0.01 to 3.0% by weight, especially 0.05 to 3.0% by weight, based on the weight of the textile fibre material, of a the compound of formula (1).

The process is usually conducted in the temperature range of from 5 to 100° C., especially 5 to 60° C. Preferred is a temperature range of 5 to 40° C., especially 5 to 35° C. and more preferably 5 to 30° C.

The detergent compositions herein will preferably be formulated such that, during use in aqueous cleaning operations, the wash water will have a pH of between about 6.5 and about 11, preferably between about 7.5 and 11. Laundry products are typically at pH 9-11. Techniques for controlling pH at recommended usage levels include the use of buffers, alkalis, acids, etc., and are well known to those skilled in the art.

Machine laundry methods herein typically comprise treating soiled laundry with an aqueous wash solution in a washing machine having dissolved or dispensed therein an effective amount of a machine laundry detergent composition in accordance with the invention. By an effective amount of the detergent composition it is meant, e.g., from 20 g to 300 g of product dissolved or dispersed in a wash solution of volume from 5 to 85 litres, as are typical product dosages and wash solution volumes commonly employed in conventional machine laundry methods. Examples are top-loading, vertical axis U.S.-type automatic washing machines using about 45 to 83 liters of water in the wash bath, a wash cycle of about 10 to about 14 minutes and a wash water temperature of about 10 to about 50° C.;

front-loading, horizontal-axis European-type automatic washing machine using about 8 to 15 liters of water in the wash bath, a wash cycle of about 10 to about 60 minutes and a wash water temperature of about 30 to about 95° C.;

top-loading, vertical-axis Japanese-type automatic washing machine using about 26 to 52 liters of water in the wash bath, a wash cycle of about 8 to about 15 minutes and a wash water temperature of about 5 to about 25° C.

The liquor ratio is preferably 1:4 to 1:40, especially 1:4 to 1:15. Highly preferred is a liquor ratio of 1:4 to 1:10, especially 1:5 to 1:9.

Using the composition according to the invention it is possible to destroy fungi present on the washing material in the dilute liquor during the washing procedure. At the same time, antifungal properties are imparted to the washed textile material, that is to say bacteria that get on the textile material while it is being worn are destroyed.

The formulations according to the invention exhibit strong fungicidal activity.

The compositions according to the invention are also used as solid soaps, dishwashing formulations or all-purpose cleaners.

A detergent has, for example, the following composition:
0.01 to 5% by weight of a compound of the formula (1),
3.0% by weight of octanol 4EO,
1.3% by weight fatty alcohol $C_8$-$C_{10}$ polyglucoside,
3.0% by weight isopropanol, and
water to 100%.

The detergent compositions of the present invention deliver to the laundry fungistatic and fungicidal properties that keeps your fabrics protected against mildew and mold. They prevent growth of molds and fungi on fabrics, protect garments against musty odor, damages in the fiber resistance and avoid formation of dark pigmented stains caused by fungi. They provide long lasting antifungal effects on fabrics even during storage under moist and warm conditions. Consequently, garments will keep their freshness preserved much longer.

Furthermore, the compounds of formula (1) are also useful active agents against dust mites.

The following Examples illustrate the invention. Percentages and parts are percentages by weight and parts by weight, respectively.

EXAMPLES 1

Preparation of a Liquid Washing Formulations (1)-(5)

Liquid formulations having the following compositions are prepared:

| Formulation | 1 | 2 | 3 | 4 | 5 |
|---|---|---|---|---|---|
| Compound of formula (101) | 0.6 | 0.6 | 0.6 | 0.6 | 0.6 |

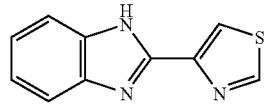

| (Thiabendazol) | | | | | |
|---|---|---|---|---|---|
| sodium dodecylbenzenesulfonate | 6 | 6 | 6 | 6 | 6 |
| sodium lauryl sulfate | 8 | 8 | 8 | 8 | 8 |
| Pareth 45-7 (Dobanol 45-7) | 4 | 4 | 4 | 4 | 4 |
| ethanol | 9 | 9 | 9 | 9 | 9 |
| sodium cumenesulfonate | 5 | — | 5 | 5 | — |
| soap noodles (Mettler) | 5 | 7 | 7 | 5 | 7 |
| trisodium citrate dihydrate | 2 | 2 | 2 | 2 | 2 |
| triethanolamine | 5 | 5 | 5 | 5 | 5 |
| fluorescent whitening agents | 0.3 | 0.3 | 0.3 | 0.3 | 0.3 |
| water to | 100 | 100 | 100 | 100 | 100 |

EXAMPLE 2

Determination of the Anti-Fungal Efficacy of Fabric Washed with Liquid Detergents Containing the Compound of Formula (101)

Test Formulations/Liquid Detergent:
Placebo, with 0,2% and 0.3% of the compound of formula (101)
Before test begin the detergent is dissolved in 25° C. water.
Linitest with Liquid Detergent:

| Liquor ratio: | 1:20 |
|---|---|
| Fabric: | 15 g Cotton Tricot |
| Temperature: | 25° C. |
| Duration: | 10 Minutes |
| Rinsing: | twice for 30 seconds (each 1 liter water) |
| Drying: | until totally dry at room temperature |

Concentrations:
1. Cotton tricot treated with liquid detergent Placebo: 0.40 g detergent/300 ml tap water
2. Cotton tricot treated with liquid detergent+0.2% of the compound of formula (101): 0.40 g detergent/300 ml tap water (=0.2%)
3. Cotton tricot treated with liquid detergent+0.2% of the compound of formula (101): 0.60 g detergent/300 ml tap water (=0.3%)

Test Strain:
*Chaetomium globosum* ATCC 6105 (washed up agar slant)
Diluted 1:10 in sterile 0.85% saline solution+50% Sabouraud–2% glucose broth.
Each sample (4 cm discs) is inoculated with 0.5 ml fungal suspension (=final concentration on the sample: ~$10^5$ spores) and placed in a dessiccator (>90% humidity) and incubated at 28° C.

Test Time:
Visual evaluation after 1, 2, 3 and 4 weeks.
1.1.1.1.1.1 Principle:
1.1.1.1.1.2 Discs with a diameter of 4 cm are cut from the washed fabric and inoculated with 0.5 ml of the fungal suspension prepared above, given in sterile petri dishes and placed in dessiccator at 28° C. and ~90%-95% humidity.
After 1, 2, 3 and 4 weeks all samples are observed on visual growth on each sample ("black spots") and the observations written in a table.
Results (Visual Observations)

| | 2. Evaluation on "black spots" | | | |
|---|---|---|---|---|
| | *Chaetomium globosum* ATCC 6205 ($10^3$-$10^4$ spores/sample) | | | |
| 2.1.1.1 Samples | After 1 week | After 2 weeks | After 3 weeks | After 4 weeks |
| 1) Placebo liquid detergent | ++ | +++ | +++ | +++ |
| 2) Liquid detergent + 0.2% of the compound of formula (101) | − | − | (+) | (+) |
| 3) Liquid detergent + 0.3% of the compound of formula (101) | − | − | − | − |

− = no visual growth
(+) = "single spots"
++ = strong growth
+++ = very strong growth

EXAMPLE 3

Determination of the Anti-Fungal Efficacy of Fabric Washed with Detergent Bars Containing the Compound of Formula (101)

Test Samples: (Natural Soap Base)
1. Placebo detergent without the compound of formula (101)
2. Detergent bar soap containing 0.1% the compound of formula (101)
3. Detergent bar soap containing 0.05% the compound of formula (101)

Hand Washing Test with the Detergent Bar Soaps:
Textile material: 10 g Cotton Tricot
Washing Protocol:
The detergent bar is rubbed by hand on the wet fabric 5 times on each side during 1 minute. Afterwards the fabric sample is soaked and kneaded for 10 minutes, rinsed under tap water for 1 minute. Drying until totally dry at room temperature Test Strain:
*Chaetomium globosum* ATCC 6105*
A washed up agar slant is diluted: 1:10 in sterile 0.85% saline solution+0.05% Sabouraud–2% glucose broth.
Each sample (4 cm disc) is inoculated with 0.5 ml of the fungal suspension (=final concentration on the sample: ~105 cfu) and placed in a dessiccator (>90% humidity).

Test Time:
 Visual evaluation after 1, 2, 3 and 4 weeks.
2.1.1.1.1.1 Principle
 Discs with a diameter of 4 cm are cut from the washed fabric and inoculated with 0.5 ml of the fungal suspension prepared above, given in a sterile petri dishes and placed in dessiccator at 28° C. and ~90%-95% humidity.
 After 1, 2, 3 and 4 weeks all samples are observed on visual growth on each sample ("black spots") and the observations written in a table.

3. Evaluation on "black spots"

| 4.<br>4.1.1.1 Samples | Chaetomium globosum ATCC 6205 ($10^4$ spores/sample) | | | |
|---|---|---|---|---|
| | After 1 week | After 2 weeks | After 3 weeks | After 4 weeks |
| 1) Placebo detergent | ++ | +++ | +++ | +++ |
| 2) Detergent bar with 0.1% of the compound of formula (101) | − | (+) | (+) | (+) |
| 3) Detergent bar with 0.05% of the compound of formula (101) | − | (+) | (+) | (+) |

− = no visual growth
(+) = "single spots"
++ = strong growth
+++ = very strong growth

EXAMPLE 4

Determination of the Anti-Fungal Efficacy of Fabric Washed with an ECE Powder Detergent Containing the Compound of Formula (101)

Test Samples:
1. Placebo=ECE Detergent powder (Color Fastness Detergent 77)
2. ECE Detergent powder containing 0.2% of the compound of formula (101) (*) (*) Incorporation via slurry of 0.2% of the compound of formula (101) in ECE Color Fastness Test.
Linitest with Detergent Powder

| | |
|---|---|
| Detergent concentration: | 0.4 g/300 ml tap water |
| Liquor ratio: | 1:20 |
| Fabric: | 15 g Cotton Tricot |
| Temperature: | 25° C. |
| Duration: | 10 minutes |
| Rinsing: | twice for 30 seconds (each in 1 liter water) |
| Drying: | until totally dry at room temperature |

Test Strain:
 *Chaetomium globosum* ATCC 6105
 Washed up agar slant is diluted 1:5 in sterile 0.85% saline solution+0.05% Sabouraud-2% glucose broth.
 Each sample (discs with 4 cm diameter) is inoculated with 0.5 ml of the bacterial mixture or fungal suspension (=final concentration on the sample: ~105 cfu) and placed in a dessiccator (>90% humidity).
Material:
Sterile Petri dishes (Ø55 mm)
Humid chamber
Sterile plastic Stomacher bags
Sterile forceps
Incubator 28° C.+/−1° C.

Contact Times:
 Immediately, 1, 2, 3 and 4 weeks after inoculation at 28° C.
Principle
 Discs with a diameter of 4 cm are cut from the washed fabric and inoculated with 0.5 ml of the fungal suspension prepared above, given in sterile petri dishes and placed in dessiccator at 28° C. and ~90%-95% humidity.
 After 1, 2, 3 and 4 weeks all samples will be observed on visual growth on each sample ("black spots") and the observations written in a table.
4.1.1.1.1.1.1

5. Evaluation on "black spots"

| 6.<br>6.1.1.1 Samples | Chaetomium globosum ATCC 6205 ($10^4$ spores/sample) | | | |
|---|---|---|---|---|
| | After 1 week | After 2 weeks | After 3 weeks | After 4 weeks |
| 1) Placebo Detergent Powder | ++ | ++ | +++ | +++ |
| 2) Detergent Powder with 0.2% of the compound of formula (101) | − | − | (+) | (+) |

− = no visual growth
(+) = "single spots"
++ = strong growth
+++ = very strong growth

EXAMPLE 5

Determination of the Fungicidal Efficacy of Fabric Treated with a Fabric Conditioner Containing the Compound of Formula (101)

The growth of *Chaetomium globosum*, a cause of "spots" is inhibited and even eliminated by time. On the cotton fabric rinsed with the original fabric conditioner, the growth of the mould was significant.
Test Formulations:
 0.1% of the compound of formula (101) is suspended in the fabric conditioner. The market product fabric conditioner is tested in comparison.
Treatment:

| | |
|---|---|
| Concentration: | 0.75 g fabric conditioner 180 ml tap water |
| Liquor ratio: | 1:6 |
| Fabric: | 30 g Cotton Tricot |
| Temperature: | 20° C. |
| Duration: | 5 Minutes |
| Drying: | Until totally dry at room temperature |

Determination of the Bactericidal Activity According to AATCC Test Method 100-1998 (Assessment of the Antibacterial Finishes on Textile Materials)
Samples:
1) Cotton tricot treated with fabric conditioner (placebo)
2) Cotton tricot treated with fabric conditioner+0.1% of the compound of formula (101)
Test Strain:
 *Chaetomium globosum* ATCC 6105 (washed up agar slant)
Dilution:
 1:5 in sterile 0.85% saline solution+0.05% Sabouraud-2% glucose broth. Each sample is inoculated with 0.3 ml fungal suspension (=final concentration on the sample: ~$10^5$ cfu) and placed in a dessiccator.

Materials:
Sterile petri dishes (diameter 55 mm and 90 mm)
Discs with a diameter of 4 cm
Humid chamber
Plastic bags sterile
Stomacher 80
Sterile forceps
Neutralizer:
  Sterile phosphate buffer 0.07 molar containing 1% Tween 80 and 0.3% lecithin (20 ml/Stomacher bag)
Dilution Media:
  Sterile deionized water, pH 7.4
Media:
  Mycological agar for fungal numbers (*Chaetomium globosum*)
Contact Times:
  Immediately after inoculation, after 1, 2 and 4 weeks at 28° C. and >90% humidity.
Incubation of the Plates:
  ~4-5 days at 28° C.

Principle

Discs with a 4 cm diameter are prepared and placed into sterile petri dishes (55 mm). The test samples are then inoculated with 0.30 ml of the diluted fungal suspension (about ~$10^5$ cfu/end concentration on each sample), placed in a dessiccator and incubated at 28° C.

Immediately after inoculation, after 1, 2 and 4 weeks at 28° C., the samples are placed into a sterile bag (Stomacher bag 80) containing 20 ml phosphate buffer, 0.07 molar, pH 7.4 containing 1% Tween 80 and 0.3% lecithin and treated in the Stomacher for 1 minute. After shaking 1:10 dilutions until $10^{-3}$ in sterile deionized water are made. From the un-diluted and from the dilutions, samples of 0.1 ml were given on 18 ml containing Mycological agar plates by the help of a spiral plater. All plates are placed in the incubator at 28° C. for about 4-5 days. After incubation the surviving colonies are counted and reported as cfu/sample in a table.

| | 7. Test strain | | | |
|---|---|---|---|---|
| | *Chaetomium globosum* ATCC 6205 ($4.7 \times 10^6$/ml) | | | |
| 7.1.1.1 Samples | 0' | 1 week | 2 weeks | 4 weeks |
| 1) Cotton tricot treated with fabric conditioner (placebo) | $2.4 \times 10^4$ $2.5 \times 10^4$ | No growth visible | $3.9 \times 10^4$ $1.3 \times 10^4$ | $6.1 \times 10^5$ $8.5 \times 10^4$ |
| 2) Cotton tricot treated with fabric conditioner + 0.1% of the compound of formula (101) | — — | No growth visible | <100* <100* | <100* <100* |

*Chaetomium globosum* ATCC 6205: $4{,}7 \times 10^6$/ml

Conclusion

Strong antifungal activity can be observed after 2 and 4 weeks contact time with the cotton sample treated with Market fabric conditioner containing 0.1% of the compound of formula (101) against *Chaetomium globosum*.

EXAMPLE 6

Preparation of Further Liquid Washing Formulations

| Components | Formulation | | | | | | | | | | |
|---|---|---|---|---|---|---|---|---|---|---|---|
| | 12a | 12b | 12c | 12d | 12e | 12f | 12g | 12h | 12i | 12k | 12l |
| Composition comprising 30% of the compound of formula (101) and 70% of propylene glycol | 0.6 | 0.6 | 0.6 | 0.6 | 0.6 | 0.6 | 0.6 | 0.6 | 0.6 | 0.6 | 0.6 |
| compound of formula (102) [HO, Cl—phenyl—O—phenyl—Cl structure] | 0.9 | 0.9 | 0.9 | 0.9 | 0.9 | 0.9 | 0.9 | 0.9 | 0.9 | 0.9 | 0.9 |
| dodecylbenzenesulfonic acid | 7.5 | | | | | | | 8.5 | | | |
| sodium dodecylbenzenesulfonate | | 27 | 23.6 | 10 | 28 | | | | 20 | 24 | 6 |
| sodium laureth sulfate 3 EO | 17 | 10 | | | | | | | | | |
| sodium lauryl sulfate | | | | | | 6 | | | | | 8 |
| coconut acid | 12.5 | | | 10 | 4 | 4 | 10 | | | 10 | |
| $C_{12\text{-}13}$ Pareth-7 | 10 | | | | | | | 26.9 | 27.8 | 25 | 4 |
| PEG-7 $C_{13}$ oxoalcohol | | | | 20 | 9 | 14.5 | 12 | 29 | 26 | | |
| PEG-8 $C_{13\text{-}15}$ fatty alcohol | | | | | | | 10 | | | | |
| alkyl polyglucoside | | | 5 | | | 1 | 2 | | | | |
| lareth-10 | | 5 | | | | | | | | | |
| PPG | | | | 2 | 3 | 8 | | | | | |
| sodium carbonate | | | 2 | | | | | | | | |
| sodium tripolyphosphate | | | 20 | | | | | | | | |
| potassium tripolyphosphate 50% | | 22 | | | | | | | | | |
| sodium cumenesulfonate 40% | | | 25 | | | | | | | | |
| trisodium citrate | 5.5 | | | | | 2 | | | | | 2 |
| lauryltrimonium chloride | 0.7 | | | | | | | | | | |
| polycarboxylate | | | | 13 | 18 | 15 | 10 | 23 | 16.2 | | |
| 2-propanol | 6 | | | 7 | 3 | | 4 | 9.5 | 8 | | |
| ethanol | 6 | | | | | | | | | | 9 |
| glycerol | | | | | | | | | | 20 | |
| propylene glycol | | | | | | | | | | 6 | |
| NaOH | 3.2 | | | 2 | 1 | 2.3 | 1.8 | 1.1 | | 1.8 | 4 |

-continued

| Components | Formulation | | | | | | | | | | |
|---|---|---|---|---|---|---|---|---|---|---|---|
| | 12a | 12b | 12c | 12d | 12e | 12f | 12g | 12h | 12i | 12k | 12l |
| fluorescent whitening agent Tinopal CBS-x | 0.1 | 0.1 | 0.1 | 0.1 | 0.1 | 0.1 | 0.1 | | | | 0.1 |
| fluorescent whitening agent Tinopal CBS-CL | | | | | | | | 0.1 | 0.1 | 0.1 | |
| Soap | | | | | | | | | | | 7 |
| water to | 100 | 100 | 100 | 100 | 100 | 100 | 100 | 100 | 100 | 100 | |

EXAMPLE 7

Preparation of Different Formulations

| components | formulation | | |
|---|---|---|---|
| | 13a | 13b | 13c |
| combination of 30% of the compound of formula (101) and 70% of propylene glycol | 0.6 | 0.6 | 0.3 |
| compound of formula (102) | 0.9 | 0.9 | 0.45 |
| sodium laureth sulfate | 1.2 | | |
| cocamidopropyl betaine | 1 | | |
| lauramine oxide | 1 | | |
| sodium Citrate | 4 | | |
| sodium carbonate | 3 | | |
| ethanol | 3 | | |
| sodium $C_{14-17}$ alkyl sec. Sulfonate | | 16.6 | |
| sodium laurylsulfate | | 20 | |
| Laureth-09 | | | 3 |
| sodium cumolsulfonate | | | 5 |
| sodium chloride | | | 3 |
| Quaternium 18 and iospropylalcohol | | | 4 |
| Pareth-25-7 | | | 0.5 |
| water to | 100 | 100 | 100 |

What is claimed is:

1. A method for the fungicidal treatment of textile fiber material comprising contacting said textile fiber materials in a domestic washing process with a detergent composition comprising
    (a) 0.01 to 90% by weight of a compound of formula (1)

(1)

wherein
R₁ is hydrogen; or $C_1$-$C_5$alkyl
    (b) 1 to 80% by weight of one or more synthetic detergents or of a soap or combinations thereof;
    (c) 0-75% of a builder;
    (d) 0-30% by weight of a peroxide;
    (e) 0-10% by weight of a bleach activator;
    (f) 0 to 50% by weight of one or more hydrotropic agents,
    (g) 0 to 50% by weight of an alcohol,
    (h) 0 to 80% by weight of a fabric softening component;
    (i) tap water or deionised water ad 100% and
    (k) an antimicrobial agent,
    wherein the component (k) is
    2-hydroxy-diphenyl ether of formula (4)

or (5)

and
wherein said textile fiber materials are treated in normal washing machines and the weight of the textile material to water is from 1:4 to 1:40.

2. A method according to claim 1, wherein
$R_1$ is hydrogen.

3. The method according to claim 1, wherein the detergent composition comprises
    (a) 0.01 to 10% by weight of a compound of formula (1);
    (b) 5 to 70% by weight of one or more synthetic detergents or of a soap or combinations thereof and/or of a salt of a saturated and/or unsaturated $C_8$-$C_{22}$ fatty acid,
    (f) 0 to 50% by weight of one or more hydrotropic agents,
    (g) 0 to 50% by weight of an alcohol,
    (h) 0 to 80% by weight of a fabric softening component; and
    (i) tap water or deionised water ad 100%.

4. The method according to claim 1, wherein component (b) is a salt of lauric, myristic, palmitic, stearic, arachidic, behenic, caproleic, dodecenoic, tetradecenoic, octadecenoic, oleic, eicosenoic or erucic acid.

5. The method according to claim 1, wherein the detergent composition comprises
    (a) 0.01-5% of a compound of formula (1);
    (b) 1-70% of an anionic surfactant and/or a nonionic surfactant;
    (c) 0-75% of a builder;
    (d) 0-30% of a peroxide; and
    (e) 0-10% of a bleach activator.

6. The method according to claim 5, wherein the detergent composition comprises,
    (a) 0.01-5% of a compound of formula (1);
    (b) 5-70% of an anionic surfactant and/or a nonionic surfactant;
    (c) 5-70% of a builder;
    (d) 0.5-30% of a peroxide; and
    (e) 0.5-10% of a bleach activator and/or 0.1-2% of a bleaching catalyst.

7. The method according to claim 1 wherein the detergent composition additionally comprises at least one enzyme selected from the group consisting of cellulase, protease, amylase and lipase.

8. The method according to claim 7, wherein the temperature of the water is between 5° C. and 40° C. throughout the process.

9. The method according to claim 1 in which the textile materials are polyamides, wool or cotton.

10. The method according to claim 1, wherein the detergent composition is used in powder washing formulations, washing pastes, liquid washing formulations, fabric softeners or solid soaps.

11. The method according to claim 1, wherein component a) is 0.01 to 5% by weight and component (k) is a maximum of 0.9% by weight 2-hydroxy-diphenyl ether of formula

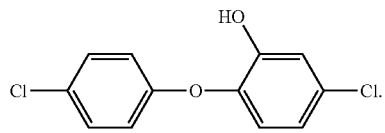

(5)

* * * * *